US012063900B2

(12) United States Patent
Lefers et al.

(10) Patent No.: US 12,063,900 B2
(45) Date of Patent: Aug. 20, 2024

(54) LIQUID DESICCANT BASED HUMIDITY PUMP, EVAPORATIVE COOLER, AND AIR PURIFICATION SYSTEMS

(71) Applicant: KING ABDULLAH UNIVERSITY OF SCIENCE AND TECHNOLOGY, Thuwal (SA)

(72) Inventors: Ryan Michael Lefers, Thuwal (SA); Mark Alfred Tester, Thuwal (SA); TorOve Leiknes, Thuwal (SA); Peiying Hong, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 712 days.

(21) Appl. No.: 17/263,293

(22) PCT Filed: Jul. 24, 2019

(86) PCT No.: PCT/IB2019/056332
§ 371 (c)(1),
(2) Date: Jan. 26, 2021

(87) PCT Pub. No.: WO2020/026084
PCT Pub. Date: Feb. 6, 2020

(65) Prior Publication Data
US 2021/0289717 A1 Sep. 23, 2021

Related U.S. Application Data

(60) Provisional application No. 62/757,350, filed on Nov. 8, 2018, provisional application No. 62/711,890, filed on Jul. 30, 2018.

(51) Int. Cl.
*A01G 9/24* (2006.01)
*A61L 9/20* (2006.01)
*F24F 3/14* (2006.01)

(52) U.S. Cl.
CPC ............. *A01G 9/246* (2013.01); *A61L 9/20* (2013.01); *F24F 3/1417* (2013.01); *A61L 2209/16* (2013.01)

(58) Field of Classification Search
CPC ............. F24F 3/1417; F24F 5/0035; F24F 2203/1032; F24F 3/14; A01G 9/246; A01G 9/24; A61L 9/20; A61L 2209/16
See application file for complete search history.

(56) References Cited

U.S. PATENT DOCUMENTS

| 3,840,145 A | 10/1974 | Almanza |
| 4,803,846 A | 2/1989 | Assaf |

(Continued)

FOREIGN PATENT DOCUMENTS

| CN | 1343292 A | 4/2002 |
| CN | 101014807 A | 8/2007 |

(Continued)

OTHER PUBLICATIONS

Office Action in corresponding/related Colombian Application No. NC2021/0001456, dated Oct. 27, 2022.

(Continued)

*Primary Examiner* — Edelmira Bosques
*Assistant Examiner* — Brett Peterson Mallon
(74) *Attorney, Agent, or Firm* — PATENT PORTFOLIO BUILDERS PLLC

(57) ABSTRACT

A liquid desiccant system for controlling a temperature inside an enclosure includes a liquid desiccant evaporative cooler (LDEC) system configured to cool down an incoming air stream (AA) entering the enclosure by using a first liquid desiccant; a liquid desiccant humidity pump (LDHR) system configured to remove humidity from a humid air stream (AD) that exists the enclosure by using a second liquid desiccant; and a storage system fluidly connected to the (Continued)

LDEC system and to the LDHR system and configured to separately store the first liquid desiccant and the second liquid desiccant. The humid air stream (AD) includes water vapors from the first liquid desiccant and from inside the enclosure.

17 Claims, 13 Drawing Sheets

(56) References Cited

U.S. PATENT DOCUMENTS

| | | | |
|---|---|---|---|
| 5,797,272 | A | 8/1998 | James |
| 6,012,296 | A | 1/2000 | Shah |
| 6,264,836 | B1 | 7/2001 | Lantis |
| 6,324,860 | B1 | 12/2001 | Maeda et al. |
| 6,843,835 | B2 | 1/2005 | Fornai et al. |
| 6,976,365 | B2 | 12/2005 | Forkosh et al. |
| 7,938,888 | B2 | 5/2011 | Assaf |
| 8,769,971 | B2 | 7/2014 | Kozubal et al. |
| 8,834,614 | B2 | 9/2014 | Ball et al. |
| 9,337,840 | B2 | 5/2016 | Son et al. |
| 9,696,048 | B2 | 7/2017 | Goldsworthy et al. |
| 9,982,901 | B2 | 5/2018 | Mongar |
| 10,006,648 | B2 | 6/2018 | Vandermeulen et al. |
| 10,024,558 | B2 | 7/2018 | Vandermeulen |
| 2002/0116934 | A1 | 8/2002 | Dinnage et al. |
| 2004/0031282 | A1 | 2/2004 | Kopko |
| 2004/0099140 | A1 | 5/2004 | Hesse et al. |
| 2005/0263003 | A1 | 12/2005 | Fornai et al. |
| 2012/0125020 | A1 | 5/2012 | Vandermeulen et al. |
| 2012/0294794 | A1 | 11/2012 | Pelin |
| 2013/0056177 | A1 | 3/2013 | Coutu et al. |
| 2014/0223947 | A1 | 8/2014 | Ranjan et al. |
| 2014/0245769 | A1 | 9/2014 | Vandermeulen et al. |
| 2014/0260372 | A1 | 9/2014 | Woods et al. |
| 2015/0047382 | A1 | 2/2015 | Jappen et al. |
| 2015/0107287 | A1 | 4/2015 | Forkosh |
| 2015/0260420 | A1 | 9/2015 | Forkosh |
| 2018/0169571 | A1 | 6/2018 | Stuckenberg |
| 2018/0177140 | A1* | 6/2018 | Gallant ............... A01G 9/24 |

FOREIGN PATENT DOCUMENTS

| | | |
|---|---|---|
| CN | 102165268 A | 8/2011 |
| CN | 102667350 A | 9/2012 |
| CN | 104813107 A | 7/2015 |
| CN | 104981282 A | 10/2015 |
| CN | 105121965 A | 12/2015 |
| CN | 105588236 A | 5/2016 |
| CN | 106918104 A | 7/2017 |
| CN | 107003078 A | 8/2017 |
| CN | 107110525 A | 8/2017 |
| CN | 114413356 A | 4/2022 |
| CO | 14064347 | 3/2014 |
| CO | 14085793 | 4/2014 |
| CO | 15072388 | 3/2015 |
| EP | 0517432 A1 | 12/1992 |
| GB | 2548590 A | 9/2017 |
| JP | S53122548 A | 10/1978 |
| JP | S58201922 A | 11/1983 |
| JP | 2004526931 A | 9/2004 |
| JP | 2005233435 A | 9/2005 |
| JP | 2010197006 A | 9/2010 |
| JP | 2011015655 A | 1/2011 |
| JP | 2013100987 A | 5/2013 |
| JP | 2017003214 A | 1/2017 |
| JP | 2017517395 A | 6/2017 |
| KR | 20130055952 A | 5/2013 |
| KR | 1020140022777 A | 2/2014 |
| KR | 101525610 B1 | 6/2015 |
| RU | 2233243 C1 | 7/2004 |
| RU | 2328334 C1 | 7/2008 |
| RU | 2562858 C2 | 9/2015 |
| WO | 2004078322 A1 | 9/2004 |
| WO | 2007066212 A2 | 6/2007 |
| WO | 2011062808 A1 | 5/2011 |
| WO | 2017176114 A1 | 10/2017 |
| WO | 2019089971 A1 | 5/2019 |

OTHER PUBLICATIONS

Office Action in corresponding/related Eurasian Patent Application No. 202190173, date stamped Oct. 7, 2021.
First Examination Report in corresponding/related Saudi Arabian Application No. 522433169, issued Sep. 27, 2022.
First Examination Report in corresponding/related Saudi Arabian Application No. 521421145, issued Mar. 31, 2022.
Dai, Y., et al., "Study on Heat and Mass Transfer Process of Solar Liquid Desiccant Dehumidifying Potential Storage," Journal of Engineering Thermophysics, Sep. 10, 2001, vol. 22, Issue 5, pp. 606-608.
First Examination Report in corresponding/related Indian Application No. 202117005021, dated Aug. 12, 2022.
Notification on Grant of Patent Right for Invention in corresponding/related Chinese Application No. 201980060275.5, dated Aug. 15, 2022.
Notice of Reason for Rejection in corresponding/related Japanese Patent Application No. 2021-505423, issued Apr. 3, 2023.
Second Office Action in corresponding/related Eurasian Patent Application No. 202190173, dated Jan. 25, 2022.
International-Type Search Report from the Eurasian Patent Office in corresponding/related Eurasian Patent Application No. 202293140, date of completion May 4, 2023.
First Office Action in corresponding/related Chinese Patent Application No. 201980060275.5, issuing date Feb. 25, 2022.
Davies, P.A., "A solar cooling system for greenhouse food production in hot climates," Solar Energy, vol. 79, Issue 6, Dec. 2005 (Available online Mar. 18, 2005), pp. 661-668.
Dean, J., et al., "Solar-Powered, Liquid-Desiccant Air Conditioner for Low-Electricity Humidity Control—Summary Report," ESTCP, Energy and Water Projects Demonstration Plan SI-0822, TP-7A40-56437-2, Nov. 2012, 41 pages.
El Hourani, M., et al., "Effective desiccant dehumidification system with two-stage evaporative cooling for hot and humid climates," Energy and Buildings, vol. 68, Part A, Jan. 2014, pp. 329-338.
Kassem, T.K., et al., "Solar Powered Dehumidification Systems Using Desert Evaporative Coolers: Review," International Journal of Engineering and Advanced Technology (IJEAT), vol. 3, Issue 1, Oct. 2013, pp. 115-128.
Kozubal, E., et al., "Desiccant Enhanced Evaporative Air-Conditioning (DEVap): Evaluation of a New Concept in Ultra Efficient Air Conditioning," National Renewable Energy Laboratory (NREL), Technical Report, NREL/TP-5500-49722, Jan. 2011, 71 pages.
Lefers, R., "A Liquid Desiccant Cycle for Dehumidification and Fresh Water Supply in Controlled Environment Agriculture," King Abdullah University of Science and Technology, Dissertation, Nov. 2017, 358 pages.
Lefers, R., et al., "Liquid desiccant dehumidification and regeneration process to meet cooling and freshwater needs of desert greenhouses," Desalination and Water Treatment, vol. 57, Oct. 2016 (Published online Apr. 19, 2016), pp. 23430-23442 (14 pages total).
Lowenstein, A., "Review of Liquid Desiccant Technology for HVAC Applications," HVAC&R Research, vol. 14, No. 6, Nov. 2008 (Published online Feb. 25, 2011), pp. 819-839 (22 pages total).
Lychnos, G., et al., "Modelling and experimental verification of a solar-powered liquid desiccant cooling system for greenhouse food production in hot climates," Energy, vol. 40, Issue 1, Apr. 2012 (Available online Mar. 16, 2012), pp. 116-130.
Mahmud, K., et al., "Performance testing of a counter-cross-flow run-around membrane energy exchanger (RAMEE) system for HVAC applications," Energy and Buildings, vol. 42, Issue 7, Jul. 2010, pp. 1139-1147.
Mohammad, A. Th., et al., "Historical review of liquid desiccant evaporation cooling technology," Energy and Buildings, vol. 67, Dec. 2013, pp. 22-33.

(56) References Cited

OTHER PUBLICATIONS

Mohammad, A. Th., et al., "Survey of hybrid liquid desiccant air conditioning systems," Renewable and Sustainable Energy Reviews, vol. 20, Apr. 2013 (Available online Jan. 2, 2013), pp. 186-200.
Öberg, V., et al., "Chapter 10: A Review of Liquid Desiccant Cooling," Advances in Solar Energy, An Annual Review of Research and Development, vol. 12, Jan. 1983, 24 pages.
PCT International Search Report (Form PCT/ISA/210) for corresponding/related International Application No. PCT/IB2019/056332, dated Mar. 26, 2020.
PCT Written Opinion of the International Searching Authority (Form PCT/ISA/237) for corresponding/related International Application No. PCT/IB2019/056332, dated Mar. 26, 2020.
Sabeh, N.C., "Evaluating and Minimizing Water Use by Greenhouse Evaporative Cooling Systems in a Semi-Arid Climate," The University of Arizona, University Libraries, UA Campus Repository, Electronic Dissertation, 2007 (Uploaded Jul. 31, 2017), 217 pages.
Seyed-Ahmadi, M., et al., "Transient behavior of run-around heat and moisture exchanger system. Part I: Model formulation and verification," International Journal of Heat and Mass Transfer, vol. 52, Issues 25-26, Dec. 2009 (Available online Sep. 8, 2009), pp. 6000-6011.
First Examination Report in corresponding/related Australian Application No. 2019313490, issued Feb. 29, 2024.
Examination Report and Search Report in corresponding/related UAE Application No. P6000155/2021, issued Dec. 26, 2023.
Office Action-Notification in corresponding/related Eurasian Patent Application No. 202293140, issued Sep. 28, 2023.
Request for the Submission of an Opinion in corresponding/related Korean Application No. 10-2021-7005832, dated Sep. 25, 2023.
Communication under Rule 71(3) EPC in corresponding/related European Application No. 19773523.6, dated Aug. 17, 2023.

* cited by examiner

LIQUID DESICCANT BASED HUMIDITY PUMP, EVAPORATIVE COOLER, AND AIR PURIFICATION SYSTEMS

CROSS-REFERENCE TO RELATED APPLICATIONS

This application is a U.S. National Stage of International Application No. PCT/IB2019/056332, filed on Jul. 24, 2019, which claims priority to U.S. Provisional Patent Application No. 62/711,890, filed on Jul. 30, 2018, entitled "LIQUID DESICCANT HUMIDITY PUMP FOR EVAPORATIVE COOLING AND WATER SAVINGS IN CONTROLLED ENVIRONMENT AGRICULTURE," and U.S. Provisional Patent Application No. 62/757,350, filed on Nov. 8, 2018, entitled "LIQUID DESICCANT HUMIDITY PUMP AND EVAPORATIVE COOLER," the disclosures of which are incorporated herein by reference in their entirety.

BACKGROUND

Technical Field

Embodiments of the subject matter disclosed herein generally relate to using a liquid desiccant based system in a controlled environment, and more specifically, to a liquid desiccant humidity pump and evaporative cooler (LDHPEC) system that uses a liquid desiccant for capturing humidity and heating the air within a controlled environment and/or a liquid desiccant air purification (LDAP) system for removing airborne particulate and/or pathogenic matter in the controlled embodiment.

DISCUSSION OF THE BACKGROUND

Liquid desiccant technology has long been applied for dehumidification of incoming air into controlled environments, and numerous research studies and commercial products have been generated utilizing this technology, see, for example, ESTPC, 2012; Kassem, 2013, Kozubal et al., 2011; Lowenstein, 2008; Mahmud et al., 2010; Mohammad et al., 2013a; Mohammad et al., 2013b; and Oberg and Goswami, 1998. However, in general, these liquid desiccant systems are primarily used for air dehumidification, not evaporative cooling, see, for example, El Hourani et al., 2014; Mahmud et al., 2010; and Seyed-Ahmadi et al., 2009. The removal of captured humidity from the desiccants is an additional process step that requires input of extra energy, usually in the form of solar or waste heat sources, and the captured humidity is discharged outside of the controlled environment. In addition, the use of liquid desiccants in agriculture for cooling controlled environments is still at the research and development stage, see, for example, Davies, 2005, Lefers, 2017, Lefers et al., 2016, and Lychnos and Davies, 2012.

Thus, the existing systems do not use the absorbed/evaporated water vapors in an integrated manner, for both increasing and decreasing the temperature of the controlled environment as dictated by the day/night conditions. Therefore, there is a need for a system that integrates the two facets of the water evaporation/absorption and/or latent heat exchange from the liquid desiccant in a controlled environment.

SUMMARY

According to an embodiment, there is a liquid desiccant system for controlling a temperature inside an enclosure. The system includes a liquid desiccant evaporative cooler (LDEC) system configured to cool down an incoming air stream (AA) entering the enclosure by using a first liquid desiccant, a liquid desiccant humidity recovery (LDHR) system configured to remove humidity from a humid air stream (AD) that exits the enclosure by using a second liquid desiccant, and a storage system fluidly connected to the LDEC system and to the LDHR system and configured to separately store the first liquid desiccant and the second liquid desiccant. The humid air stream (AD) includes water vapors from the first liquid desiccant and from other sources inside the enclosure.

According to another embodiment, there is a greenhouse having a liquid desiccant system for controlling a temperature inside the greenhouse, the greenhouse including a liquid desiccant evaporative cooler (LDEC) system attached to the greenhouse and configured to cool down an incoming air stream (AA) by using a first liquid desiccant, a liquid desiccant humidity recovery (LDHR) system attached to the greenhouse and configured to remove humidity from a humid air stream (AD) by using a second liquid desiccant, and a storage system fluidly connected to the LDEC system and to the LDHR system, the storage system being located outside the greenhouse, and configured to separately store the first liquid desiccant and the second liquid desiccant. The incoming air stream (AA) is taken from outside the enclosure, and the humid air stream (AD) includes water vapors from the first liquid desiccant and from plants located inside the greenhouse and/or from an additional water vapor source.

According to still another embodiment, there is a method for controlling a temperature inside an enclosure. The method includes turning on a pump P1 associated with a liquid desiccant evaporative cooler (LDEC) system for cooling down an incoming air stream (AA) by using a first liquid desiccant, turning on a pump P4 associated with a liquid desiccant humidity recovery (LDHR) system for removing humidity from a humid air stream (AD), which circulates through the enclosure, by using a second liquid desiccant, transferring the first liquid desiccant from the LDEC system to a storage system, transferring the second liquid desiccant from the LDHR system to the storage system, and separately storing the first liquid desiccant and the second liquid desiccant at the storage system. The incoming air stream (AA) is taken from outside the enclosure, and the humid air stream (AD) includes water vapors from the first liquid desiccant and from plants located inside the greenhouse and/or from an additional water vapor source.

According to yet another embodiment, there is a liquid desiccant air purification system that includes a medium configured to receive an incoming air stream and a liquid desiccant flow; a conduit through which the liquid desiccant flows; and a pump configured to force the liquid desiccant through the conduit and the medium so that the incoming air stream mixes with the liquid desiccant. The liquid desiccant removes particulate matter from the incoming air stream to generate an outgoing treated air stream.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to a greenhouse having a liquid desiccant humidity pump and an evaporative cooler (LDHPEC) system for controlling an internal temperature and/or humidity of the greenhouse. However, the LDHPEC system may be used not only in a greenhouse, but in any other enclosure. Some additional embodiments are discussed with regard to a liquid desiccant air purification (LDAP) system used in a controlled environment related to livestock production. However, the LDAP system can be used in any controlled environment, related to other purposes than livestock production, as for example, human habitation or plant production.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Figure 1:
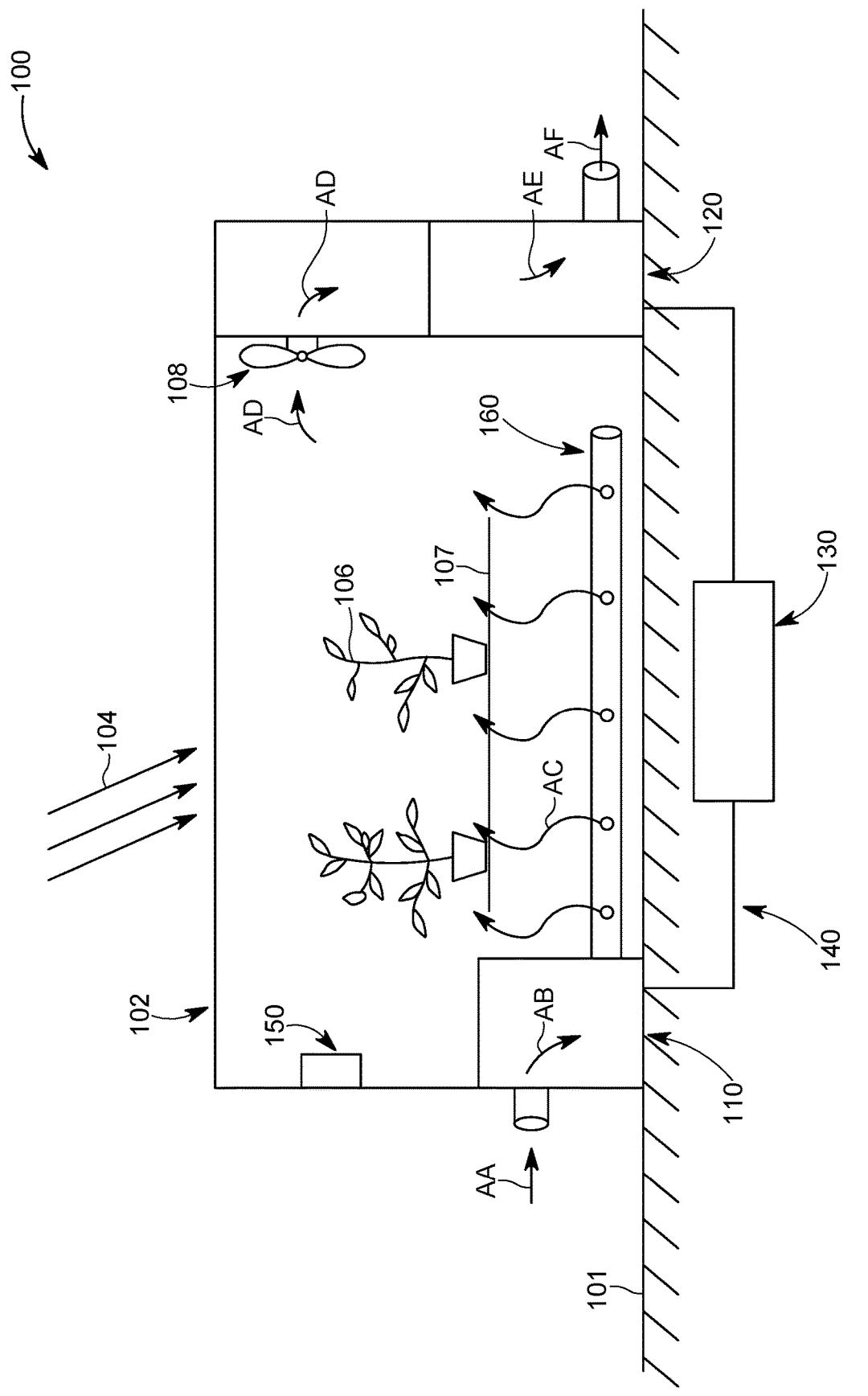
FIG. 1 illustrates a liquid desiccant humidity pump and evaporative cooler system.

According to an embodiment, there is an LDHPEC system 100 that is located next to a closed enclosure 102 (a greenhouse in this embodiment, but the system works for any enclosure), as shown in FIG. 1. The LDHPEC system 100 includes a liquid desiccant evaporative cooler (LDEC) system 110, a liquid desiccant humidity recovery (LDHR) system 120, a storage system 130, a piping system 140 that connects the LDEC system, the LDHR system, and the storage system, and a control system 150 that controls each component of the LDHPEC system 100. Each of these systems are discussed in more detail with regard to the next figures.

Ambient air AA is drawn from outside the enclosure 102 into the LDEC system 110, where it is cooled and its humidity is increased, thus resulting into an air stream AB that has a lower temperature and higher humidity than the incoming air stream AA. Cooled and humid air stream AB is released inside the enclosure 102 as air stream AC, for lowering the temperature of the enclosure during the day, when the solar waves (energy) 104 entering the enclosure is at maximum. In one application, the air stream AC is released through a discharge mechanism 160 over a large area of the enclosure 102. In one application, the discharge mechanism 160 may include various piping having corresponding holes and the piping is distributed under the bed 107 of plants 106, for releasing the air stream AC uniformly over the entire floor of the enclosure 102. Various plants 106 present inside the enclosure 102 interact with the air stream AC and release part of their humidity, which results in a high-humidity, warm air stream AD. The high-humidity, warm air stream AD is absorbed into the LDHR system 120. For this purpose, it is possible to use one or more fans 108 to move the various air streams in, out and through the enclosure 102.

The LDHR system 120 removes the humidity from the high-humidity, warm air stream AD and transforms it into a low-humidity air stream AE, which may be discharged outside the enclosure 102 as air stream AF. This process makes the air stream AE warmer. The desiccant used in both the LDEC system 110 and the LDHR system 120 is exchanged with the storage system 130 when the vapor pressure of the desiccant is smaller or larger than the vapor pressure of the corresponding air stream so that the low- or high-vapor pressure desiccant is used by each system. The storage system 130 is preferable located underground, i.e., below the Earth's surface 101. However, it is possible to locate the storage system 130 above ground. In one application, the storage system 130 is located underneath the enclosure 102 for reducing the length of the piping system 140 and also for reducing the footprint of the system. Each component system of the LDHPEC system 100 is now discussed in more detail.

Figure 2:
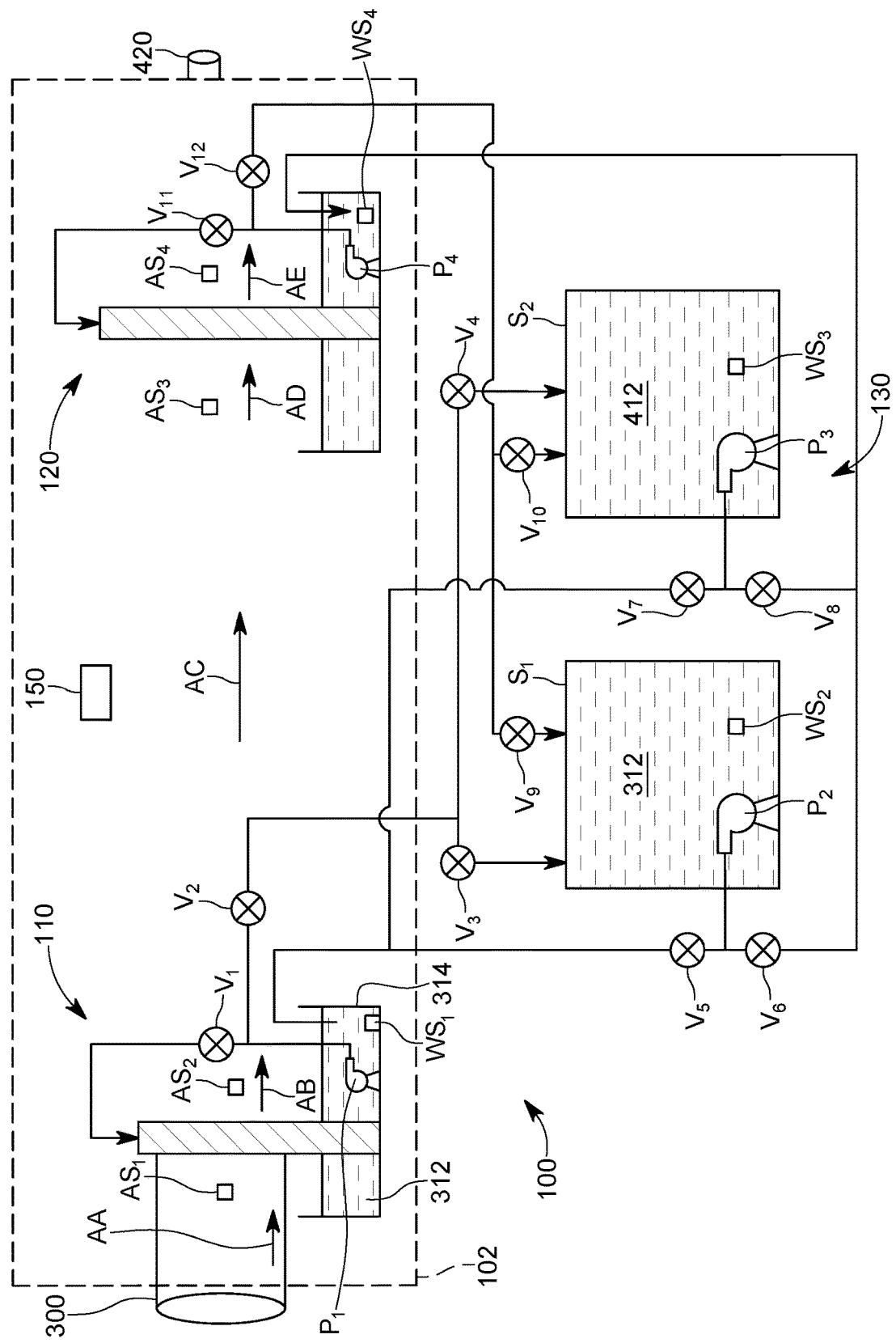
FIG. 2 illustrates details of the liquid desiccant humidity pump and evaporative cooler system.

FIG. 2 diagrammatically illustrates the various sub-systems of the LDHPEC system 100 and their fluid connections. More specifically, the air stream AA enters the LDEC system 110 at an input 300 (see FIG. 3 for more details of the LDEC system 110) and passes through a pad 310. The pad 310 has many channels (it is a porous media) that promote the movement of the air stream through it. For example, the pad may include, but is not limited to, hollow fiber membranes, flat sheet membranes, packed media beds, cardboard pads, plastic pads, etc. At the same time, the pump P1, pumps the liquid desiccant 312 from a container 314 to a top portion 310A of the pad 310, through a pipe 316. A valve V1 is provided along the pipe 316 for controlling the amount of liquid desiccant 312. Alternatively, variable speed pumps or more than one pump may be used in place at the valve. The liquid desiccant 312 flows through the channels formed into the pad 310, downward, due to gravity, and interacts with the incoming air stream AA.

The liquid desiccant 312 initially has a vapor pressure that is higher than the vapor pressure of the incoming air stream AA. Therefore, the water evaporates from the liquid desiccant, cooling both the air stream AA and the liquid desiccant 312. In addition, the humidity of the outgoing air stream AB is increased as the water vapor is transferred from the liquid desiccant 312 to the air stream AA. When the vapor pressure of the liquid desiccant 312, which is measured by sensor package WS1, located in the container 314, drops to be equal to or lower than the vapor pressure of the incoming air stream AA, which is measured by sensor package AS1 located in the inlet 300, the evaporative cooling no longer takes place. This happens after some time as the liquid desiccant 312 is continuously recirculated by the pump P1 through the pad 310 and water vapor is continually evaporated from the liquid desiccant. When this happens, the controller 150, which communicates with the sensors, valves, and pumps, instructs the liquid pump P1 to shut off. If the vapor pressure of the incoming air stream AA decreases below that of the desiccant, the controller turns on the pump P1.

At the end of the batch cycle (the batch cycle may be a full day, an hour, a half day, or any other cycle time as set by the operator), the controller 150 instructs the valve V1 to close to prevent the liquid desiccant 312 being further delivered to the pad 310 and opens valve V2 to pump with pump P1 the low-vapor pressure liquid desiccant 312 out of the LDEC system 110, to an empty storage tank S1 (see FIG. 2), which is part of the storage system 130. Controller 150 also opens valve V3 and closes valve V4 to achieve this result. Once the LDEC system 110 is empty, which is determined by the controller 150 based on measured values received from the sensor package WS1, the LDEC system 110 is refilled with high-vapor pressure liquid desiccant 412 from another full storage tank S2 (measured by sensor WS3) via pump P3. In this regard, the controller 150 stops pump P1 and starts pump P3, which is connected to the second storage tank S2. The controller 150 also closes valves V5 and V8 so that the liquid desiccant 412 from the second tank S2 is directed to container 314. The controller 150 allows the pump P3 to pump the liquid desiccant 412 for a certain time period, until the container 314 is full and/or second tank S2 is empty. The determination to use the second storage tank S2 for supplying the liquid desiccant 412 for the LDEC system 110 is made by the controller 150 only if the vapor pressure of the liquid desiccant 412 (measured with sensor WS3) is higher than the vapor pressure of the incoming air stream AA, which is measured with sensor AS1.

Note that the controller 150 can decide to empty the LDEC system 110 even before the end of the batch cycle, if, for example, the vapor pressure of the liquid desiccant 312 is smaller than the vapor pressure of the incoming air stream AA for a time longer than a given time interval, where the given time interval may take any value.

The material used for building the various elements of the LDHPEC system 100 preferably includes corrosion-resistant materials such as plastics, but the options are not limited to only plastics. This is so because the liquid desiccants 312 and 314 may be corrosive. Note that the liquid desiccant used in these embodiments may include substances that have nothing to do with salt water, brackish water or waste water. For example, the liquid desiccant may include, but is not limited to, magnesium chloride, calcium chloride, lithium bromide, etc. or the liquid desiccant may be combined with triethylene glycol, potassium acetate, etc. Note that the LDHPEC system 100 discussed herein is most appropriate for regions that lack fresh water, like desertic and semi-desertic regions, where the fresh water is at a premium. Further note that the LDHPEC system 100 discussed herein uses elements that require a minimum of electric energy, like a valve or a pump. Thus, although the LDHPEC system 100 is capable of regulating the temperature of the air inside the enclosure 102, no traditional air conditioning units are used, as these units are big electrical energy consumers. Therefore, the LDHPEC system 100 uses small amounts of electrical power and also small amounts of fresh water for conditioning the air inside the enclosure 102.

Figure 3:
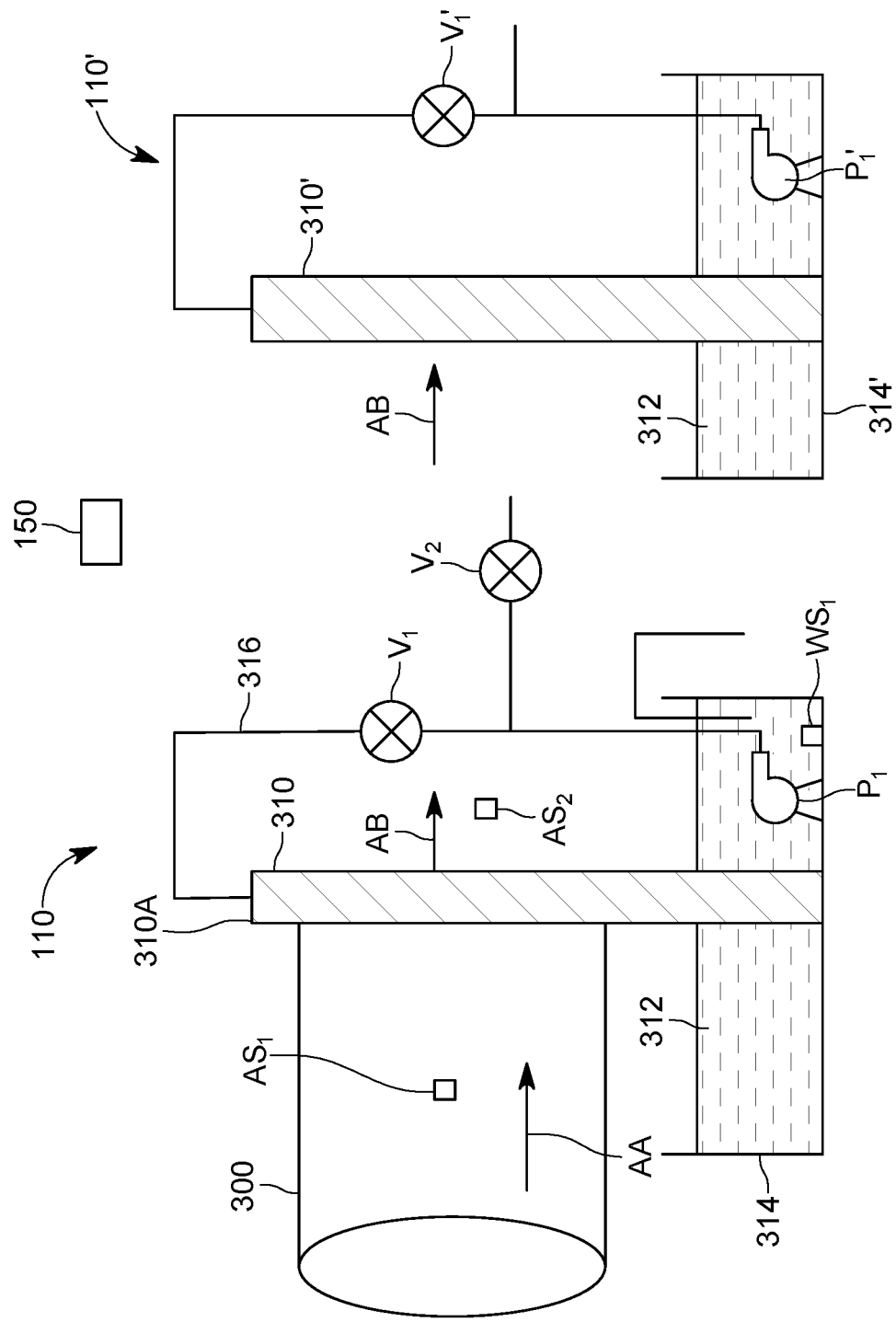
FIG. 3 illustrates a liquid desiccant evaporative cooler system of the liquid desiccant humidity pump and evaporative cooler system.

While FIG. 1 shows a single LDEC system 110 being used to cool the incoming air stream AA, it is possible to use plural LDEC systems 110 for achieving this goal. In one application, the plural LDEC systems 110 are connected in parallel to cool down a larger amount of incoming air. However, in another application, it is possible to connect in series the LDEC system 110 and another system 110', as shown in FIG. 3, for further decreasing the temperature of the air stream AB. The additional system 110', may include a similar pump P1', container 314' and pad 310' as the first LDEC system 110. In another application, the additional system 110' may be a traditional evaporative cooling system, different from the system 110. In still another embodiment, the additional system 110' may be modified to work as an aerosol removal system, to remove the salt aerosols in the air originating from the liquid desiccant 312. This is beneficial for protecting the indoor environment from the potential of salt aerosols entering the indoor environment. In yet another embodiment, the additional system 110' may be a traditional mechanical vapor compression or similar air chilling unit.

Figure 4:
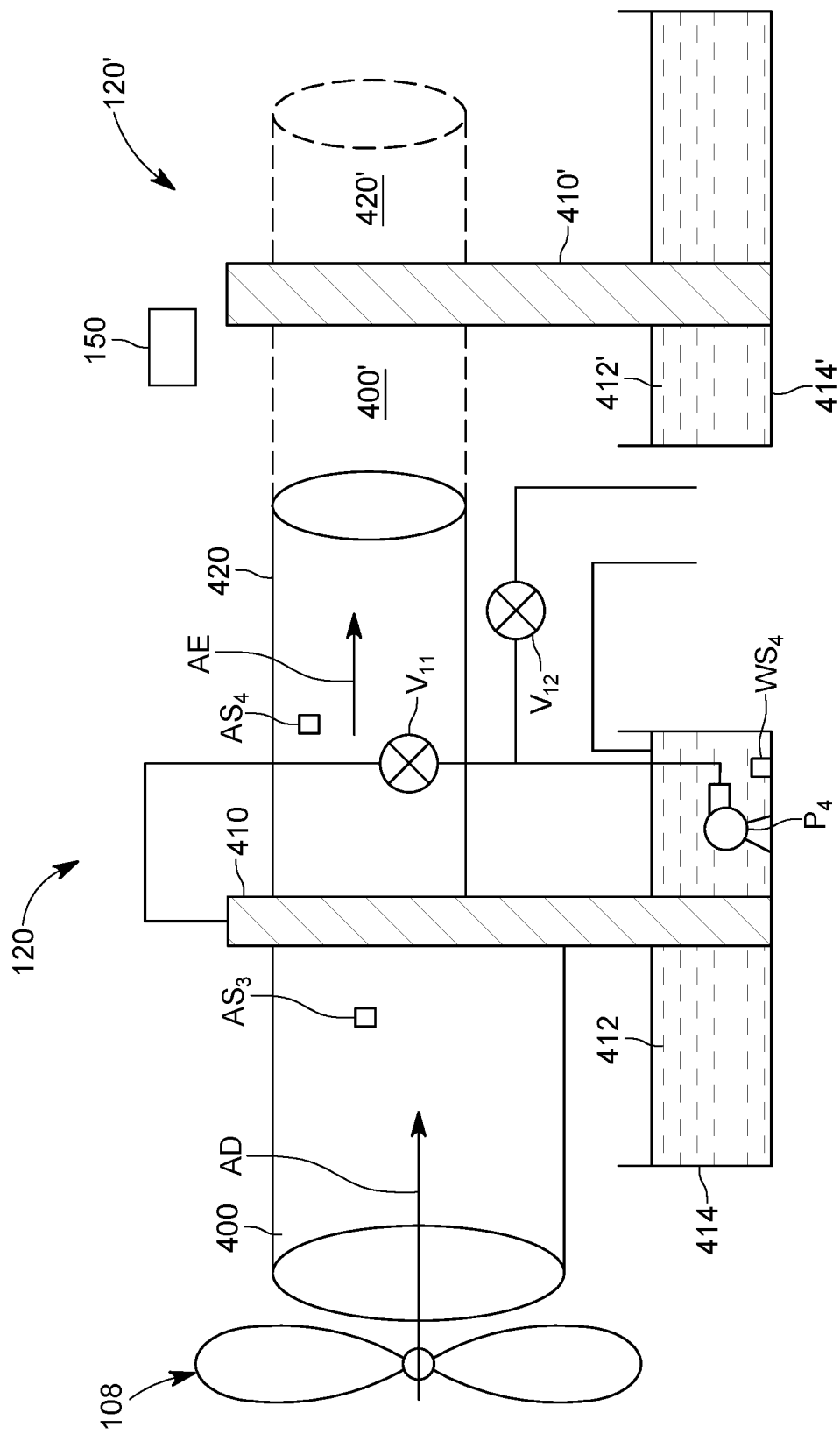
FIG. 4 illustrates a liquid desiccant humidity pump of the liquid desiccant humidity pump and evaporative cooler system.

The cooled air stream AC now interacts with the plants inside the enclosure 102 and starts gaining humidity as the plants transpire. In addition, heat is added to the air stream AC due to the heat generated by the solar radiation impacting the enclosure 102 during the day. Thus, the air stream AD entering an inlet 400 (see FIG. 4) of the LDHR system 120 is "high" in humidity and has a "high" temperature. As illustrated in FIG. 1, one or more fans 108 (or similar air movement devices) may be used to force the air through the enclosure 102, from the inlet 300 to an outlet 420 of the LDHR system 120. FIG. 4 shows the LDHR 120 having a pad 410, made of a porous material, so that air stream AD passes through the pad and exits on the other side as air stream AE, having less water vapor. A liquid desiccant 412, which is stored in a container 414, is pumped by pump P4 to the top region 410A of the pad 410 and released into the pad. The liquid desiccant 412 flows through various channels inside the pad 410, due to the gravity or pressure (depending on the system), until it returns back to container 414. During this flow, the liquid desiccant 412 interacts with the air stream AD and removes water from it, resulting in air stream AE. This is happening because the liquid desiccant 412 has a vapor pressure lower than the vapor pressure of the air stream AD. The air stream AE is then expelled from the enclosure 102 through the outlet 420. Sensors AS3 and AS4 are located inside the inlet 400 and outlet 420, respectively, for monitoring the vapor pressure of the respective air streams. Sensor WS4 is located inside the container 414 for measuring whether the liquid desiccant 412 is present. Although pump P4 is shown as being located inside the container 414, it is also possible to locate this pump outside the container.

The humidified air stream AD is cycled through the LDHR system 120 as now discussed. Initially, the LDHR system 120 contains the liquid desiccant 412 having a vapor pressure lower than that of the humid air stream AD. Therefore, as the humid air stream AD is passing through the pad 410, at the same time as the liquid desiccant 412, humidity is recovered from the air stream AD and absorbed into the liquid desiccant 412. The liquid desiccant 412 is continuously circulated by the pump P4 through the pad 410. When the vapor pressure of the liquid desiccant 412, which is measured by sensor WS4, increases to be equal with that of the humid air stream AD, which is measured by the sensor AS3, the controller 150 instructs the pump P4 to shut off. If the vapor pressure of the air stream AD increases again above the liquid desiccant 412, the controller 150 instructs the pump P4 to turn on again. At the end of the batch cycle, valve V11 is instructed by the controller 150 to close and valve V12 is instructed by the controller 150 to open to cycle the weak liquid desiccant 412 outside the container 414, to the second storage tank S2.

Returning to FIG. 2, when this step takes place, the controller 150 closes valve V9 and opens valve V10 to have the liquid desiccant 412 flowing into the second tank S2. When the liquid desiccant 412 has been removed from the container 414, as measured by sensor WS4, the controller 150 starts the pump P2 of the first storage tank S1, opens the valve V6 and closes the valves V5 and V8 to pump the liquid desiccant 312, from the first storage tank S1, which has a vapor pressure lower than the vapor pressure of the humid air AD, to refill the container 414.

In this way, the controller 150 uses the first and second tanks S1 and S2 to alternately provide the liquid desiccant for the LDEC system 110 and the LDHR system 120, in a sense swapping the liquid desiccant 312 with the liquid desiccant 412 as each liquid is either low or high in vapor pressure. The low-vapor pressure desiccant 312 in the first storage tank S1 is that which was sourced from the LDEC system 110, which means that the humidity extracted from the liquid desiccant 312 is added to the incoming air stream AA, and then it is released inside the enclosure 102, and then the same humidity is recovered from the air stream AD by the liquid desiccant 412 of the LDHR system 120, to be recycled back into the LDEC system 110 via the storage system 130.

For example, in one implementation, for a batch exchange cycle the LDEC system 110 pumps the first liquid desiccant 312 to the first storage tank S1, which is empty, then the second storage tank S2 pumps the second liquid desiccant 412 to the LDEC system 110 so that now the second storage tank S2 is empty, then the LDHR system 120 pumps the second liquid desiccant 412 to the emptied second storage tank S2, and then the first storage tank S1 pumps the first liquid desiccant 312 to the LDHR system 120, such that the LDEC system has fresh high-vapor pressure liquid desiccant, the LDHR system has fresh low-vapor pressure liquid desiccant, the first storage tank S1 is empty, and the second storage tank S2 contains high-vapor pressure liquid desiccant at the end of the batch exchange cycle.

Similar to the embodiment shown in FIG. 3, for the LDEC system 110, the LDHR system 120 in FIG. 4 may include a second unit 120', which may be connected in series or parallel to the first unit. The second unit 120' may be configured to act as a LDHR system, or as an aerosol removal system.

The sensors discussed above may include one or more of a temperature sensor, relative humidity sensor, a pressure sensor, a conductivity sensor, a refractive index sensor, a density sensor, a liquid level sensor or any other sensor or a combination of these sensors.

Figure 5:
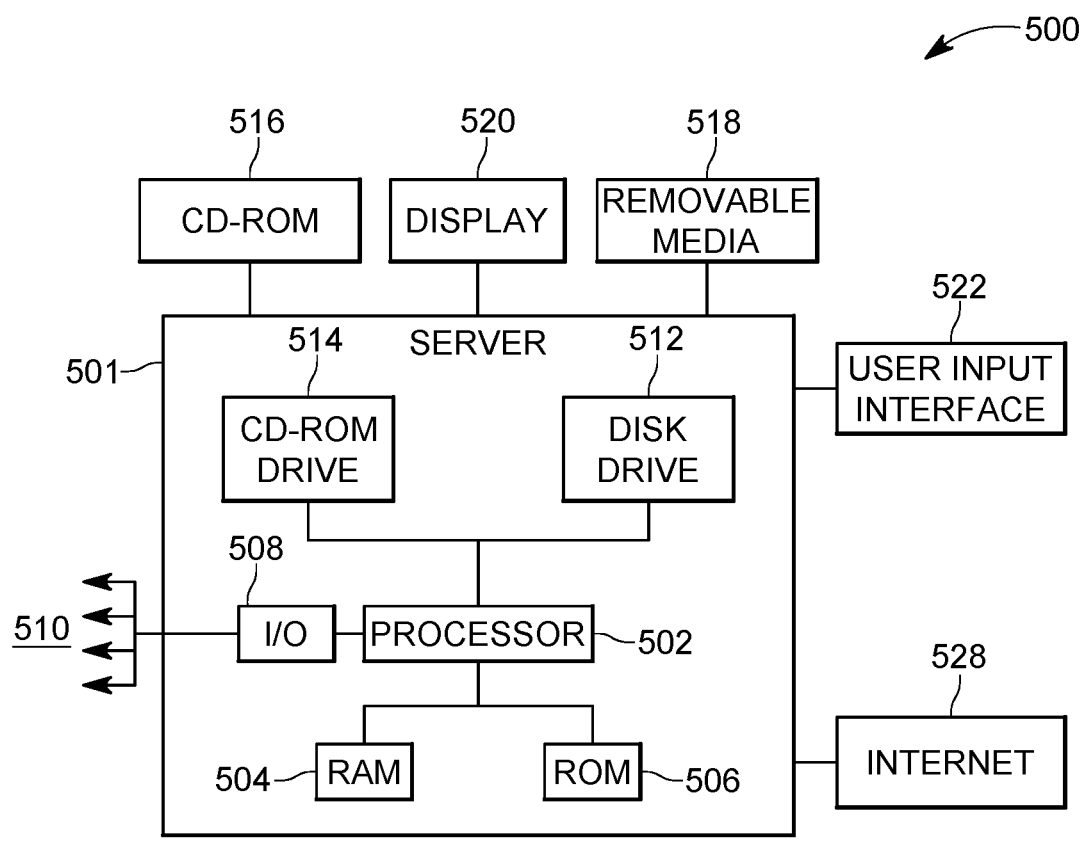
FIG. 5 illustrates a controller that controls the liquid desiccant humidity pump and evaporative cooler system.

The controller 150 may be implemented as the computing device illustrated in FIG. 5. Hardware, firmware, software or a combination thereof may be used to perform the various steps and operations described herein.

Computing device 500 suitable for performing the activities described in the exemplary embodiments may include a server 501. Such a server 501 may include a central processor (CPU) 502 coupled to a random access memory (RAM) 504 and to a read-only memory (ROM) 506. ROM 506 may also be other types of storage media to store programs, such as programmable ROM (PROM), erasable PROM (EPROM), etc. Processor 502 may communicate with other internal and external components through input/output (I/O) circuitry 508 and bussing 510 to provide control signals and the like. Processor 502 carries out a variety of functions as are known in the art, as dictated by software and/or firmware instructions.

Server 501 may also include one or more data storage devices, including hard drives 512, CD-ROM drives 514 and other hardware capable of reading and/or storing information, such as DVD, etc. In one embodiment, software for carrying out the above-discussed steps may be stored and distributed on a CD-ROM or DVD 516, a USB storage device 518 or other form of media capable of portably storing information. These storage media may be inserted into, and read by, devices such as CD-ROM drive 514, disk drive 512, etc. Server 501 may be coupled to a display 520, which may be any type of known display or presentation screen, such as LCD, plasma display, cathode ray tube (CRT), etc. A user input interface 522 is provided, including one or more user interface mechanisms such as a mouse, keyboard, microphone, touchpad, touch screen, voice-recognition system, etc.

Server 501 may be coupled to other devices, such as pumps, sensors and valves. The server may be part of a larger network configuration as in a global area network (GAN) such as the Internet 528, which allows ultimate connection to various landline and/or mobile computing devices.

While the LDHPEC system 100 discussed above is shown to include only the LDEC system 110 and the LDHR system 120, more systems may be added, as for example, a traditional air conditioning unit, a photovoltaic system, an illumination system, a cleaning system for cleaning the transparent walls of the enclosure to allow the solar energy to reach the plants, an air purification system, which is discussed later, etc.

Figure 6:
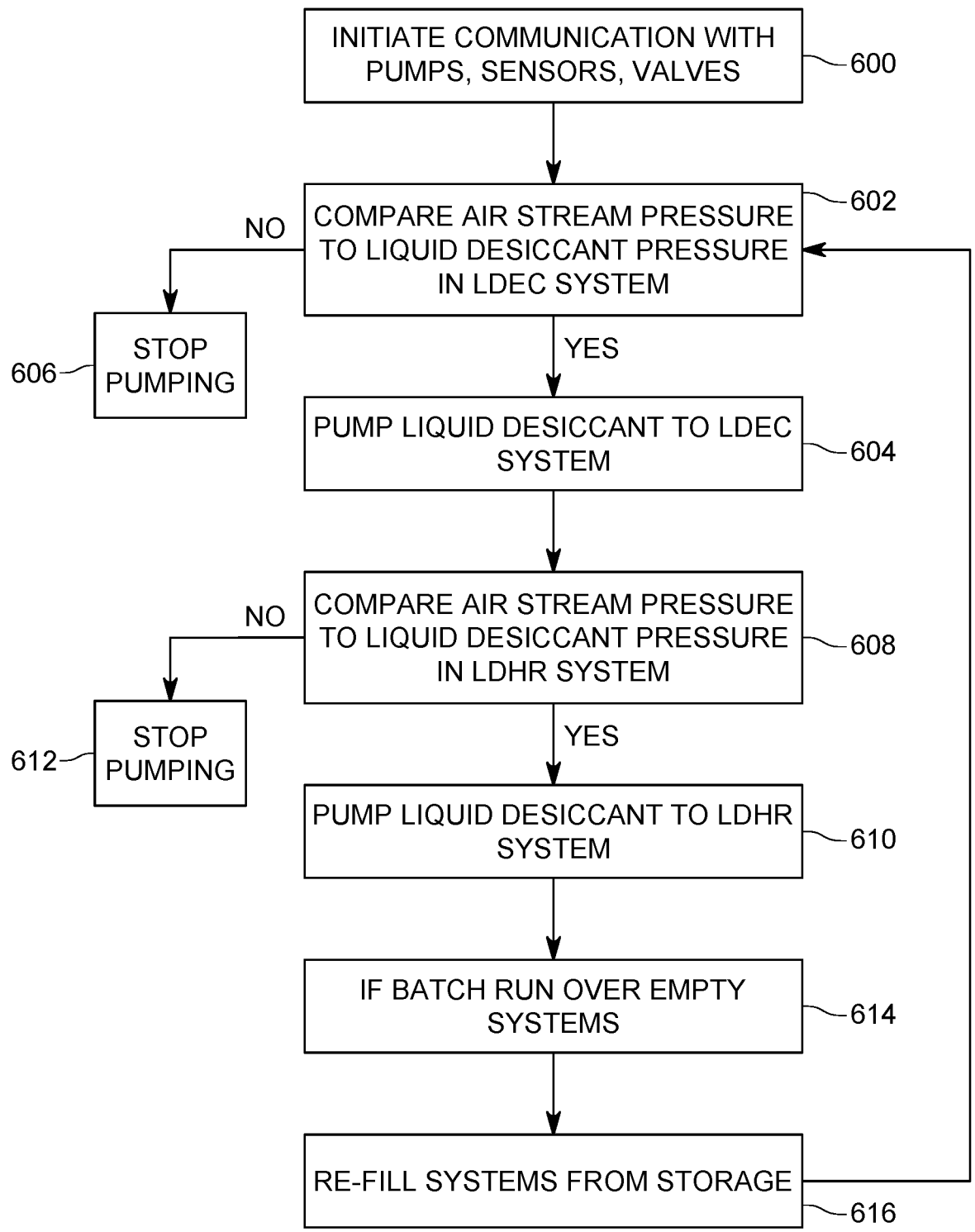
FIG. 6 is a flowchart of a method for controlling the liquid desiccant humidity pump and evaporative cooler system.

The controller 150 may be programmed to control the systems illustrated in FIG. 2 as now discussed with regard to FIG. 6. In step 600, the controller 150 communicates with each pump, sensor and valve to assign an ID to each element. In step 602, the controller receives a vapor pressure measurement from sensor AS1, of the input air stream AA, and compares it with a vapor pressure of the liquid desiccant 312, measured by sensor WS1. If the vapor pressure of the air stream AA is smaller than the vapor pressure of the liquid desiccant 312, the controller 150 turns on in step 604 pump P1, opens valve V1 and closes valve V2, to allow the liquid desiccant 312 to flow through the pad 310, and to cool and add humidity to the air stream AA. If the result of the comparing step 602 is negative, the controller turns off in step 604 the pump of the LDEC system.

Further, in step 608, the controller also receives the vapor pressure measurements of the air stream AD entering the LDHR system 120 and of the liquid desiccant 412 flowing through the LDHR system 120 and compares these vapor pressures. If the vapor pressure of the air stream AD is larger than the vapor pressure of the liquid desiccant, the controller switches on the pump P4 of the LDHR system 120 and the valve V11 that controls the flow of the liquid desiccant to the system, and closes the valve V12 that removes the liquid desiccant from the LDHR system in step 610. However, if the vapor pressure of the air stream AD is lower than the vapor pressure of the liquid desiccant, the controller switches off the pump of the LDHR system 120 in step 612. In step 614, if the batch run of either the LDEC or LDHR system is over or a certain condition was met (for example, the vapor pressure of the liquid desiccant 312 is smaller than the vapor pressure of the incoming air stream AA for a time longer than a given time interval, where the given time interval may take any value), the controller 150 opens valve V2 and/or V12 and closes valves V1 and V11 for emptying the liquid desiccant of one or both of the systems 110 and 120. Note that the two systems 110 and 120 may operate simultaneously or sequentially or alternately. The liquid desiccant from each system 110 and 120 is emptied in a corresponding storage tank S1 and S2, respectively, through valves V2 and V3 for the LDEC system and valves V12 and V10 for the LDHR system. Then, in step 616, the controller 150 may decide to re-fill one or both of the systems 110 and 120 with a different liquid desiccant, for example, the LDEC system 110 with liquid desiccant 412 from the second storage tank S2 and the LDHR system 120 with liquid desiccant 312 from the first storage tank S1. In this way, the liquid desiccant discharged by one system is reused by the other system and vice versa. Then, the process returns to step 602 to measure again the vapor pressure of the incoming air stream and outgoing air stream and the liquid desiccants in both systems and the process repeats itself. The controller 150 may be programmed to run this cycle only during the day, only during the night, both day and night, or for any desired period of time.

While the above process describes using the proposed LDHPEC system in hot and dry climates to provide cooling and humidification of the air for the indoor environment, the described system can be reversed to provide heating and dehumidification of cold and wet air for the indoor environment. The selection of whether to cool and humidify the air or to heat and dehumidify the air will depend upon the set desired conditions in the indoor environment, the local climate, and the temperature and humidity of the air to be conditioned (which may include outdoor air, recycled indoor air, or any combination of the two).

A model was created to estimate the percentage of humidity contributed to the evaporative cooling process by the LDEC system 110 and a TEC system 110' to estimate the amount of water that might be saved by implementing the LDHPEC system 100 in a dry and hot climate. The monthly average climate (temperature and humidity) of Riyadh, Saudi Arabia, from October 2012 to September 2013 was used as a base for the model. Of special importance are the warmer months of April-October, where evaporative cooling is used extensively to maintain cool temperatures for controlled environment agriculture. The model was developed for a greenhouse with a length of 40 m, width of 10 m, and a height of 3 m. The evaporative cooling efficiency of the LDEC system 110 was estimated at 0.75 and of the TEC system 110' at 0.80. The humidity recovery efficiency of the LDHR system 120 was estimated at 0.75. For the average existing greenhouses within the Kingdom of Saudi Arabia, the estimated yield of tomatoes is 30 kg/m2 per year and the estimated water footprint is 350 L/kg of tomato produced (based on a presentation by Prof. Abdulaziz alHarbi of King Saud University at the Global Forum for Innovations in Agriculture in Abu Dhabi, UAE on Feb. 5, 2018); or about 875 liters per m$^2$ of greenhouse per month. For greenhouses in hot and dry climates, it is estimated that the evaporative cooler contributes to 80-90% of the total water consumption of the agricultural system (see, Lefers et al., 2016, and Sabeh, 2007). Using the developed model, it was estimated that the LDEC system 110 will contribute about 75-80% of the total evaporative cooling water use, which is approximately 60-75% of the total greenhouse water use. Based upon the model, the LDHPEC system 100 is estimated to save approximately 45,000 to 50,000 m$^3$ of water per hectare of greenhouse installed in Saudi Arabia. When the water savings are valued at the price of desalinated water (i.e., about \$2.50/m$^3$), it is estimated that a total value of \$125,000 per hectare of greenhouse per year in water savings can be realized using the LDHPEC system 100. The estimated total production area of greenhouses in Saudi Arabia in 2015 was 3,019 hectares. Therefore, if this system is applied to only 10% of the existing greenhouses, a total value of water savings could be achieved exceeding \$37 million dollars per year.

The described system captures humidity from the air exiting the enclosure and "pumps" it back to the air entering the enclosure for evaporative cooling by utilizing a liquid desiccant. The system may run in reverse, to heat and dehumidify air of an enclosure, again utilizing liquid desiccants. Most importantly, the discussed system may save a large amount of water that is needed for a traditional greenhouse in a hot and dry climate. In reverse, the system may save energy to be used for heating or dehumidification.

Figure 7:
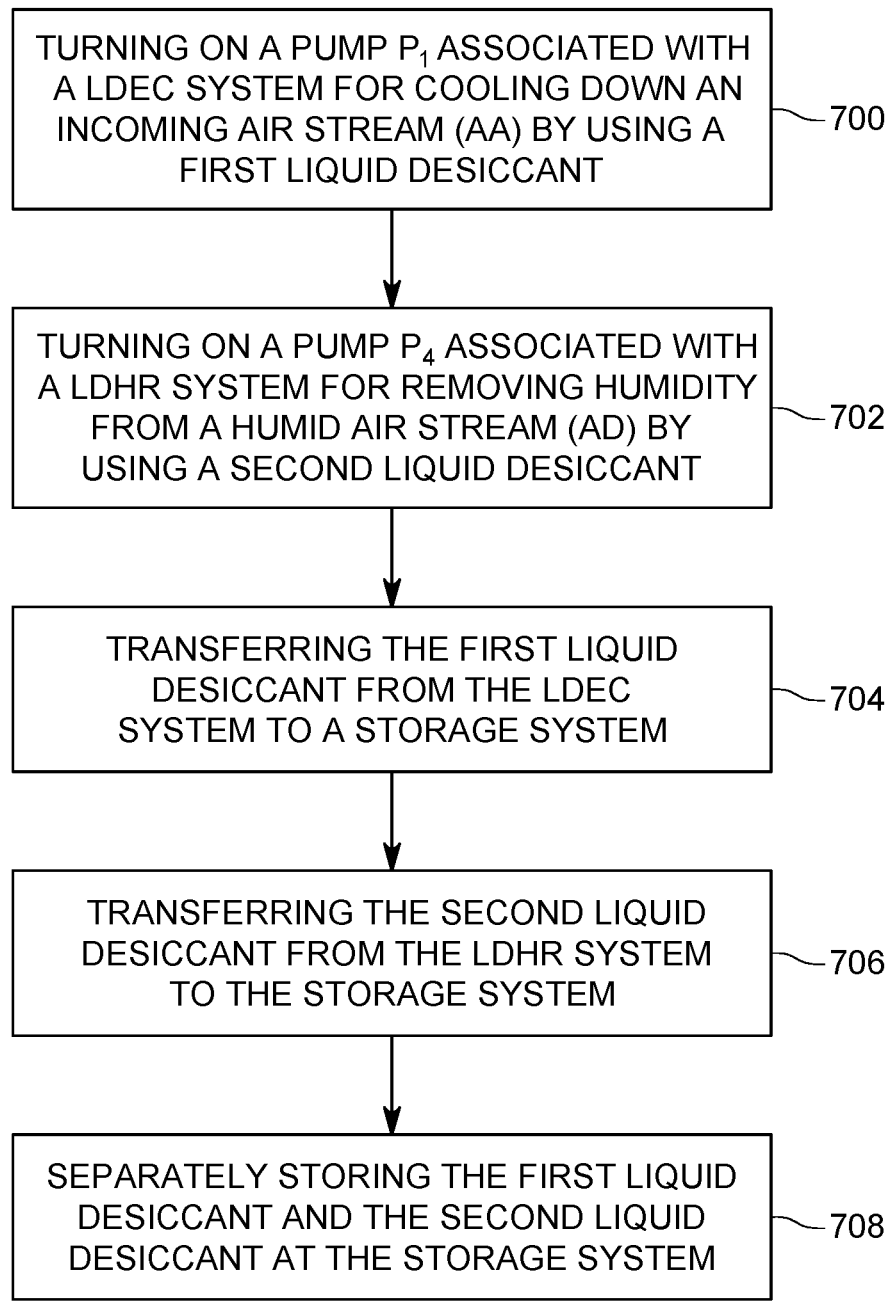
FIG. 7 is a flowchart of a method for controlling a temperature inside of an enclosure that is associated with the liquid desiccant humidity pump and evaporative cooler system.

A method for controlling a temperature inside a greenhouse as discussed above, may include, as illustrated in FIG. 7, a step 700 of turning on a pump P1 associated with a liquid desiccant evaporative cooler (LDEC) system 110 for cooling down an incoming air stream (AA) by using a first liquid desiccant 312, a step 702 of turning on a pump P4 associated with a liquid desiccant humidity recovery (LDHR) system 120 for removing humidity from a humid air stream (AD) by using a second liquid desiccant 412, a step 704 of transferring the first liquid desiccant 312 from the LDEC system 110 to a storage system 130, a step 706 of transferring the second liquid desiccant 412 from the LDHR system 120 to the storage system 130, and a step 708 of separately storing the first liquid desiccant 312 and the second liquid desiccant 412 at the storage system 130. The incoming air stream (AA) is taken from outside the enclosure, and the humid air stream (AD) includes water vapors from the first liquid desiccant (312) and from plants located inside the greenhouse. In one application, the first liquid desiccant from the storage system is fed to the LDEC system and the second liquid desiccant from the storage system is fed to the LDHR system. The method may further include comparing, with a controller, a reading from one sensor of plural sensors, which is indicative of a vapor pressure in the incoming air stream, with a reading from another sensor of the plural sensors, which is indicative of a vapor pressure of the first liquid desiccant, and determining to switch off a pump associated with the LDEC system, and/or comparing, with a controller, a reading from one sensor of plural sensors, which is indicative of a vapor pressure in the humid air stream, with a reading from another sensor of the plural sensors, which is indicative of a vapor pressure of the second liquid desiccant, and determining to switch off a pump associated with the LDHR system.

In addition to the potential to control humidity and temperature with a liquid desiccant based system, the liquid desiccants offer a unique opportunity for air purification to help control the spread of diseases, airborne spores, pollen, and dust/particulate removal. The high salt concentration of the liquid desiccants (for example, as high as 40% by weight, and about 10 times saltier than the seawater) is lethal to many strains of microorganisms and fungal spores. Further, airborne dust and other particulates can be effectively removed by liquid desiccant systems via direct air/liquid contact, when implemented into scrubbers, pad and fan systems, and packed media beds.

As disease-causing microorganisms may be attached to the airborne dust and particulates, the removal of this dust from the airstream aides in preventing the spread of disease. This process is needed for many applications, especially for the controlled environment poultry industry, which has seen recently large mortality events in chickens as a result of disease transfer between farms and poor sanitation practices on farms. It is also of importance to the plant-production industry, which is subject to disease and pathogenic fungus transfer via airborne dust, spores, and microorganisms.

However, traditional industrial scrubbers utilize fresh water in their operations. This fresh water both cools and adds humidity to the treated air due to a vapor pressure difference between the liquid water and the air below the saturation point (below 100% relative humidity). The cooling and humidifying of the air stream desired for air purification is not always desirable, and water resources are consumed as the water must be continuously replenished in the purification unit due to evaporative losses. This makes the existing fresh water based systems undesirable for scrubbing of particulates from air streams in cold climates, in systems with a desire to keep the humidity levels below a certain value, and/or areas of water scarcity or limited water access. In addition, the use of fresh water in scrubbers does not purify the air of microorganisms; these systems only remove particulates and may even contribute to the spread of diseases like *Legionella*.

Contrary to these problems of the existing air purifiers, the novel LDAP system to be discussed next offers one or more of the following benefits when compared to the freshwater-based air purifiers: (1) removes pollutants without changing the thermal properties of the air and its humidity, (2) saves fresh water, and/or (3) the desiccated, high-salt liquid condition does not favor the proliferation of pathogens, e.g., *Legionella*.

Regarding the first benefit of the novel LDAP system, i.e., it can purify the air without affecting the thermal properties of the air (in climates where this is desirable.), because the liquid desiccants can have vapor pressures equal to the ambient air, the system can remove pollutants from air in a scrubbing fashion without changing the thermal properties of the air. This is an important advantage over normal freshwater scrubbers, especially in conditioned indoor environments. The proposed use of liquid desiccants instead of fresh water in these systems allows for tailoring of the liquid desiccant such that the vapor pressure of the desiccant matches or nearly matches the vapor pressure of the air stream being treated. In such a way both the evaporation and collection of water vapor from/into the desiccant solution is minimized and the air stream being treated can be purified without an increase or decrease in its humidity.

In situations where a certain humidity set point is desired (such as 50% relative humidity), the liquid desiccant solution can be prepared to condition the air stream via evaporation or condensation of the liquid desiccant from/into the desiccant solution, depending upon the original and desired condition of the air stream being purified. Once the vapor pressure of the air matches the vapor pressure of the liquid desiccant, evaporation and/or condensation of water vapor from/into the desiccant ceases while the desiccant continues to purify the air stream. As such, the desiccant systems do not require continuous replenishment of water into the system and may in theory be operated without ever needing to replace the desiccant solution, assuming there are no faults in the system (leaks, etc.)

In addition to water savings and the potential to modify/keep the air streams to/at a desired humidity level, the liquid desiccant based systems offer the potential to purify the air of multiple forms of air pollutants, including microorganisms. The potential to purify the air of potential pathogens makes the LDAP systems very attractive for decreasing the incidence and spread of disease and contaminated air to/in/from controlled environments.

Figure 8:
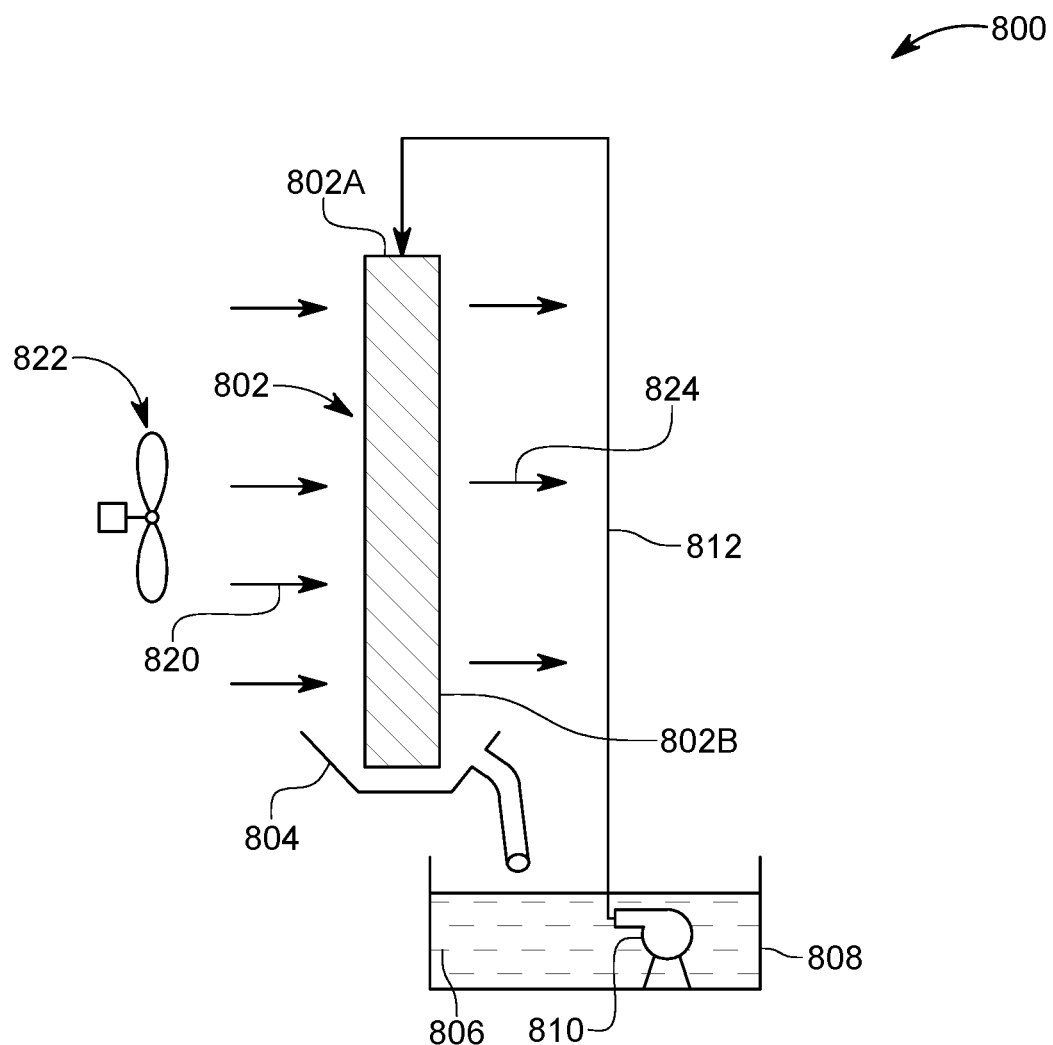
FIG. 8 illustrates a liquid desiccant based air purification system that uses a pad and fan principle.

According to an embodiment illustrated in FIG. 8, the LDAP system can be implemented as a pad and fan system 800, which includes a pad 802 supported above a tray 804. A liquid desiccant 806 is stored in a tank 808 and pumped with a pump 810, through a conduit 812, to a top portion 802A of the pad 802. The liquid desiccant 806 flows through the pad 802 due to the gravity, and is collected in the tray 804 at a bottom 802B of the pad, from which it is returned to the tank 808. The untreated air stream 820 is forced by a fan 822 (or equivalent mechanism) to enter through the pad, and thus, interacts by direct contact with the liquid desiccant 806. As a result of this interaction, various impurities and pathogens are transferred to the liquid desiccant and thus, they are removed from the untreated air stream 820, which results in a treated air stream 824. The pad 802 can have the same structure as the pad 310 discussed above.

Figure 9:
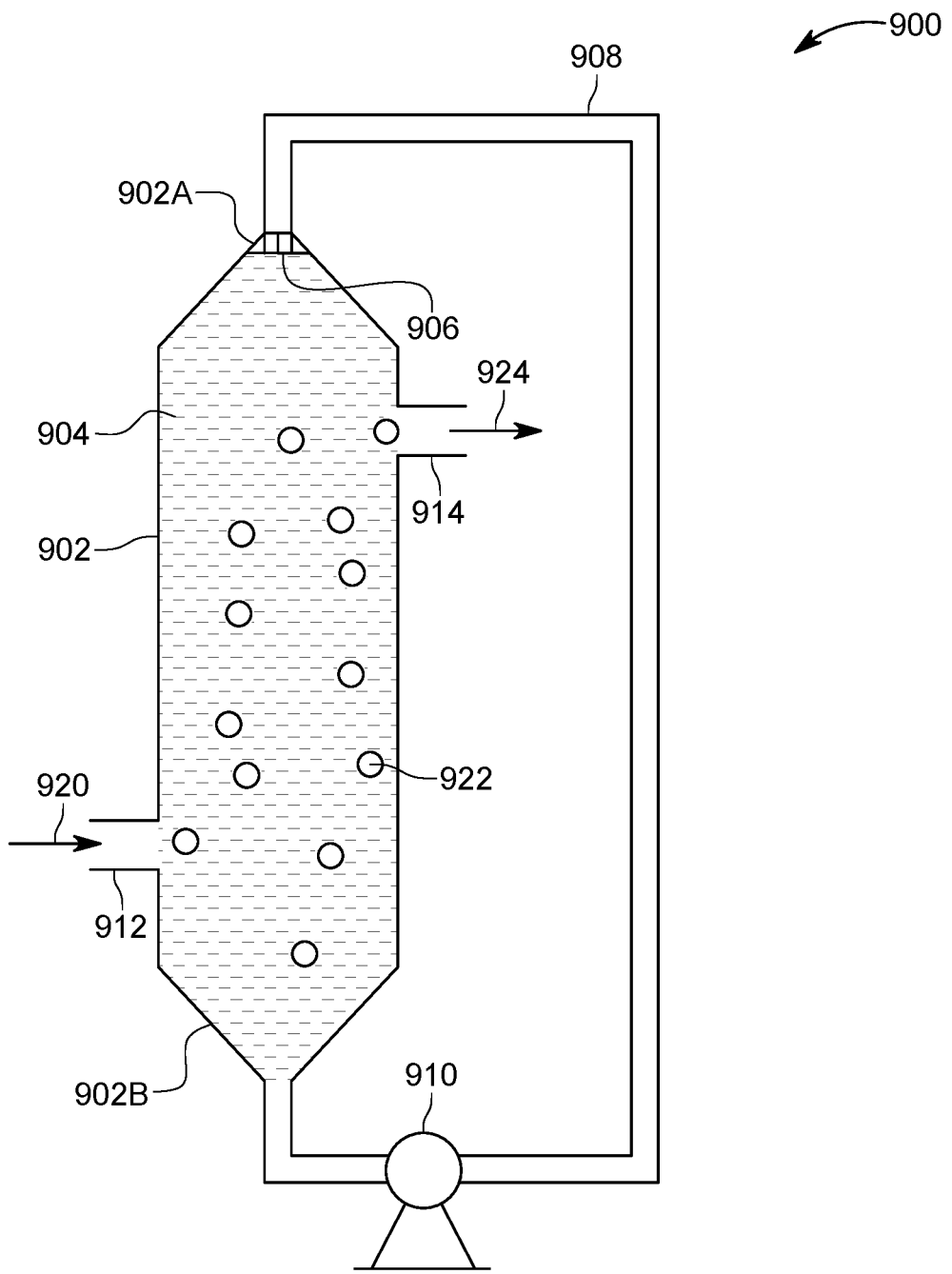
FIG. 9 illustrates a liquid desiccant based air purification system that uses a scrubber principle.

FIG. 9 shows another implementation of the LDAP system, as a scrubber system 900. The scrubber system 900 includes a body 902 that is configured to receive at a top end 902A the liquid desiccant 904, from a sprinkler 906. The sprinkler 906 is fluidly connected to a pipe 908, that carries the liquid desiccant 904 from a pump 910. The pump 910 is fluidly connected to a bottom 902B of the body 902, and the pump circulates the liquid desiccant through the closed circuit made by the pipe 908 and the body 902. A stream 920 of untreated air is inserted into the body 902 at an input 912. After the air particles 922 directly interact with the liquid desiccator 904, a treated air stream 924 is exiting the body 902 at an output 914. As in the previous embodiment, due to the direct interaction between the air particles and the liquid desiccant particles, various impurities and pathogens are transferred to the liquid desiccant and thus, they are removed from the untreated air stream 920, which results in the treated air stream 924.

Figure 10:
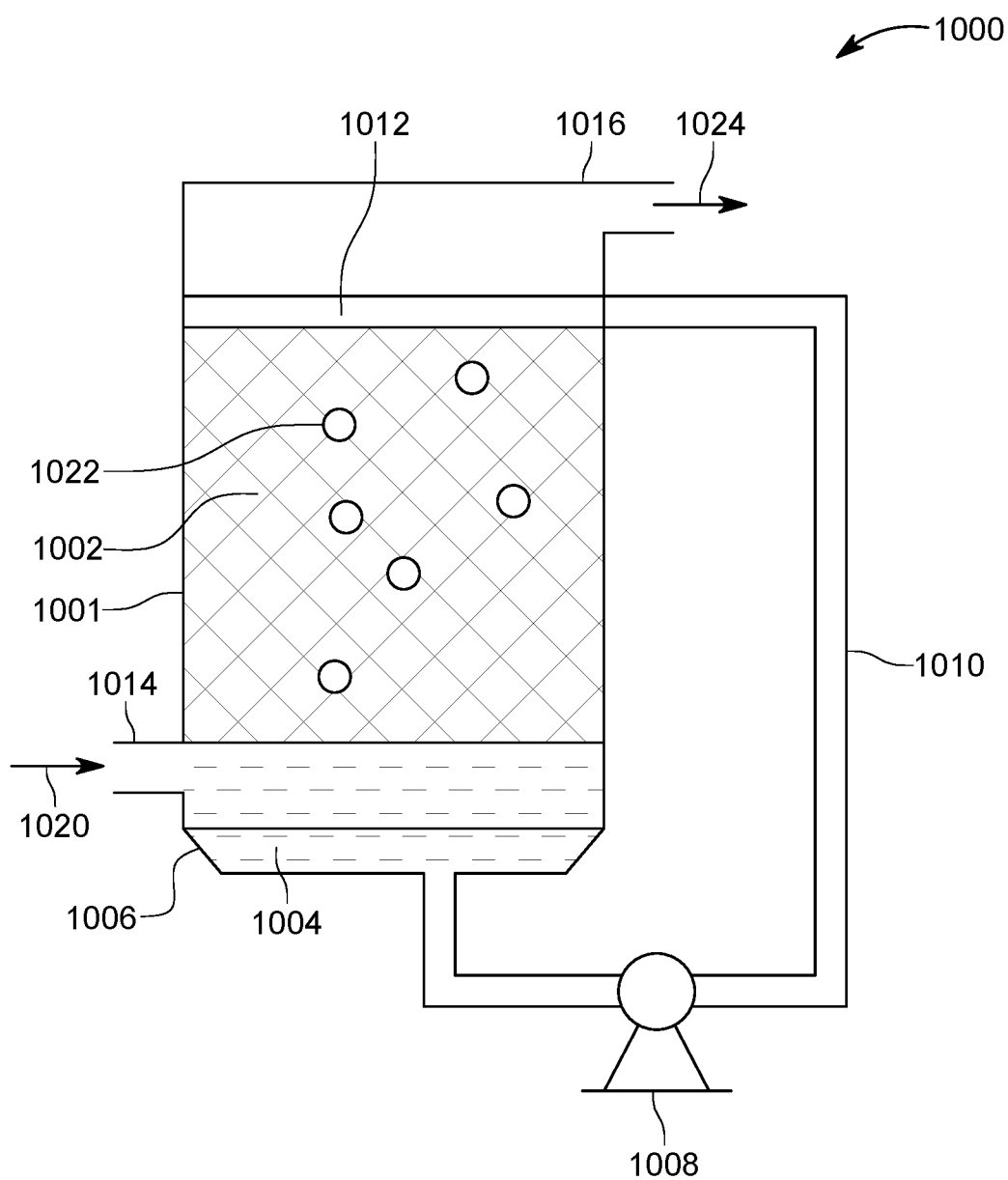
FIG. 10 illustrates a liquid desiccant based air purification system that uses a packed media principle.

Another possible implementation of the LDAP system is shown in FIG. 10, and this implementation uses a packed media bed system 1000. The packed media 1002 may be made by the same material as the pad 802. In this system, the liquid desiccant 1004 from a tray/container 1006 is pumped with a pump 1008, through a pipe 1010, to a distribution device 1012, which is placed at the top portion of the packed media 1002. The packed media 1002 is hold by gravity to the body 1001 of the system 1000. The particles of the liquid desiccant fall, due to the gravity, through the packed media 1002 and directly interact with air particles 1022 from an untreated air stream 1020. The untreated air stream 1020 enters the body 1001 at an inlet 1014, that is placed below the packed media 1002. The air particles 1022 move in an upward direction through the packed media 1002 and exit at outlet 1016 as a treated air stream 1024. The liquid desiccant 1004 is then collected at the tray 1006 and recirculated by the pump 1008. As in the previous embodiments, due to the direct interaction between the air particles and the liquid desiccant particles, various impurities and pathogens are transferred to the liquid desiccant and thus, they are removed from the untreated air stream 1020, which results in the treated air stream 1024.

Any of the LDAP systems discussed above (note that other implementations of this system may also be used) use the liquid desiccant to purify an incoming untreated airstream, for example, in controlled environment agriculture. Contaminated air is drawn into contact with the liquid desiccant in any of the systems shown in FIGS. 8 to 10, and the liquid desiccant removes the airborne pollutants via direct air/liquid contact, with additional disinfection processes.

As dust and solids continue to accumulate in the liquid desiccant system during the recirculating process of the liquid desiccant, either the dust need to be filtered/removed from the liquid system to allow continuous operation, or the entire liquid stream need to be replaced. Removal of the dust from the liquid desiccant system may be realized via a cartridge filter, membrane system, sand filter, vortex filter, or similar filtration device (this list is not intended to be exhaustive). Removal of the dust from the liquid stream allows the LDAP system to continue operation without replacing the desiccant solution.

Figure 11:
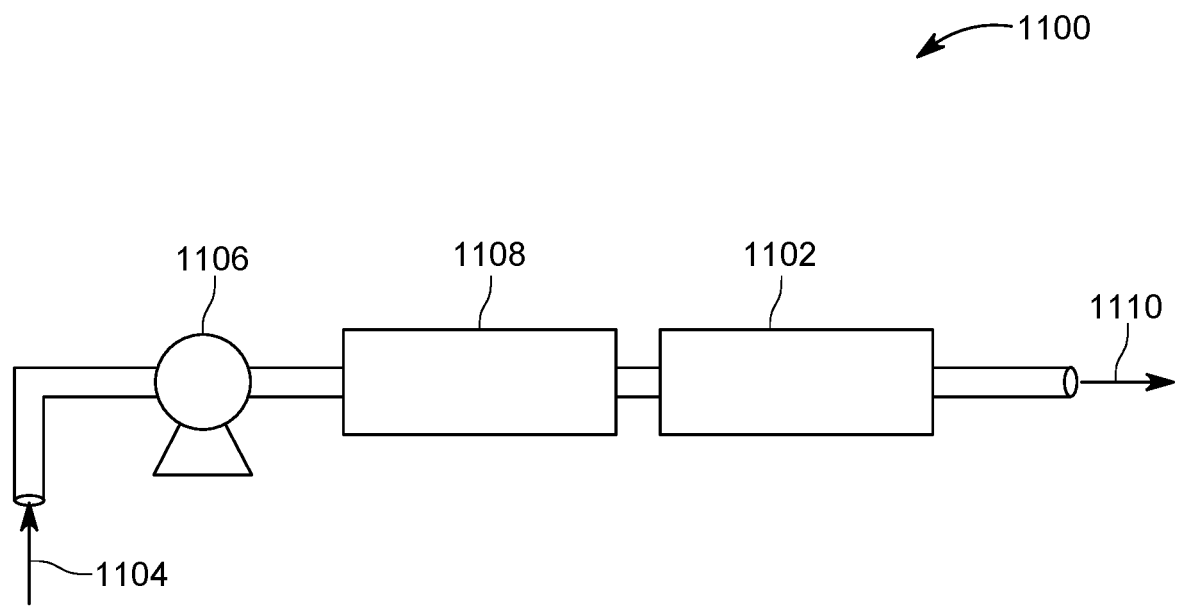
FIG. 11 illustrates a configuration of the liquid desiccant based air purification system that removes solid matter from the liquid desiccant and kills pathogens.

One such potential placement of a filtration device 1102 for removal of collected solids from an incoming liquid desiccant stream 1104 is shown in FIG. 11 for an LDAP system 1100. Those skilled in the art would understand that other placements are possible and may be realized in other embodiments of the system. The system 1100 also includes a pump 1106 that forces the liquid desiccant through the various elements. The pump 1106 may be fluidly connected to a UV treatment module 1108, which is configured to disinfect the liquid desiccant and kill organism that may survive in the hypersaline conditions of the desiccant. The elements shown in FIG. 11 may be fluidly connected to each other in any order. The liquid desiccant output stream 1110 is then ready to be provided to any of the systems 800, 900, or 1000 discussed above. In one application, the pump 1106 is the pump shown in each of the systems 800, 900, or 1000 and the filtration device 1102 and the UV treatment module 1108 are added along the pipes 812, 908, or 1010.

As microorganisms accumulate in the LDAP system, some are killed by the high salinity of the liquid desiccant in the solution and/or resulting high osmotic pressure, which may lead to lysis of the microorganism cells and/or other lethal processes. Others, however, may remain viable and may be later reintroduced to the air stream if and when their populations exceed a certain critical value. Although these microorganisms may survive in the salty, high osmotic pressure conditions of the liquid desiccant, they may be killed or rendered inviable via the use of ultraviolet (UV) light provided by the UV treatment module 1108. In one application, the UV light may be supplied to the system via a UV lamp of the UV treatment module 1108. However, in one application, the UV treatment module 1108 simply exposes the passing solution to natural sunlight, which includes UV light. An inline UV lamp has a smaller footprint, but requires electricity to operate. Natural sunlight requires no electricity, but may require a larger footprint.

The LDAP system may be configured different from a traditional fresh water air purification device in the sense that the liquid storage area will be designed to resist corrosion and to accommodate a fluctuation in the volume of the liquid desiccant, as the ambient air humidity and resulting liquid volumes change.

Figure 12:
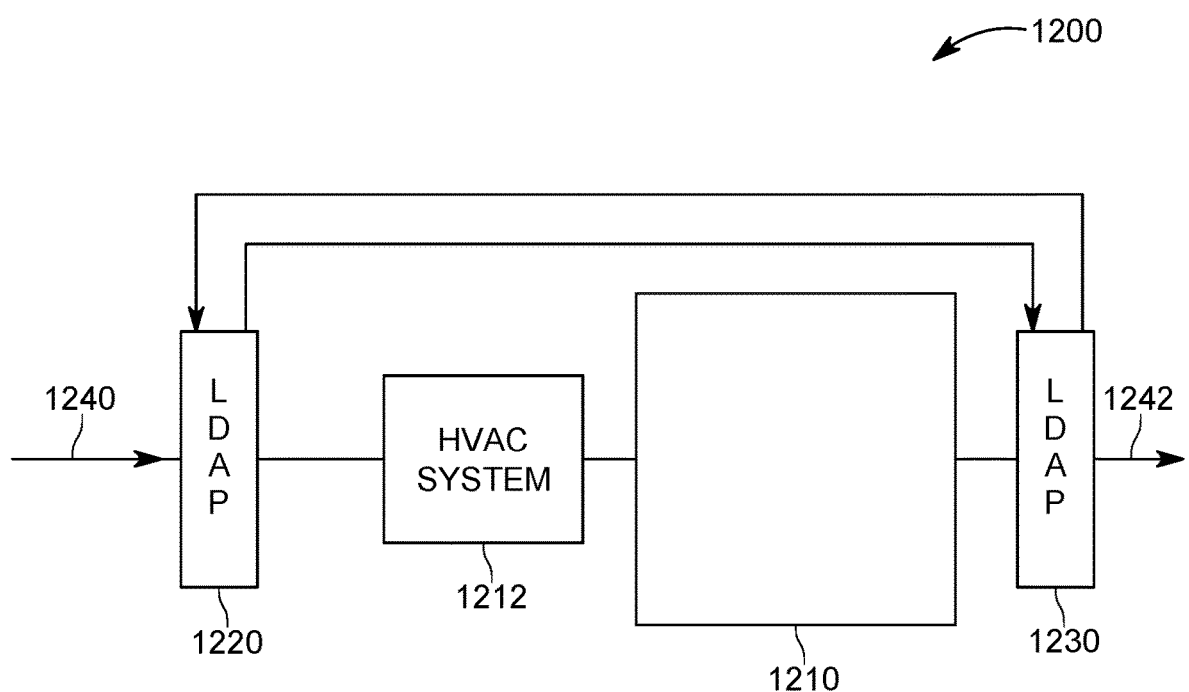
FIG. 12 illustrates a configuration in which the liquid desiccant based air purification system is integrated with a liquid desiccant based air cooling system for conditioning the air inside a chamber.

In addition to air purification, the LDAP system may also be used to thermally condition the incoming air stream via evaporative cooling, desiccant heating, dehumidification, and/or heat/energy exchange. By placing one or more LDAP systems at the inlet and outlet of a building's HVAC system, latent and sensible heat exchange can be realized to precondition the outdoor air and to reduce the load on other HVAC components. Such a system can collect sensible and/or latent heat and cooling from the outlet of the system and recycle that conditioning to the air inlet in a single-pass type of HVAC system, where indoor air is continuously being replaced by outdoor air. In this regard, FIG. 12 shows such a system 1200 that includes a controlled environment chamber 1210 that is connected to a HVAC system 1212. The chamber 1210 is understood herein to include any controlled environment structure, regardless if the structure is used for human habitation, animal growth, or crop yield. An incoming air stream 1240 is first treated by a first LDAP system 1220 (can be any of the systems 800, 900 or 1000 discussed above), then it is cooled by the HVAC system 1212 and then it is provided to the chamber 1210. In this embodiment, chamber 1210 can be a barn or similar enclosure where animal stock is held. An air stream exiting from the chamber 1210 is then treated by a second LDAP system 1230, and the outgoing air stream 1242 is released into the ambient. This latent heat exchange process is described in more detail in the embodiments illustrated in FIGS. 1-4.

The LDAS systems 1220 and 1230 are installed on a single-pass type of HVAC system 1200, where the indoor air is continuously being replaced by outdoor air. Such a system purifies both the incoming and outgoing air to protect both the animals or crop in the controlled environment chamber 1210 and also to stop the spread of any disease or pollution outside of the chamber 1210. In addition, when the liquid desiccant is cycled between the inlet and outlet of the chamber 1210 (i.e., between the first and second LSAD systems as shown in FIG. 12), the system functions as a heat/cold exchanger to reduce the load on the other HVAC system components. Thus, the system 1200 shown in FIG. 12 has the first LDAP system at the air inlet and serves to reduce the pathogen and dust load coming into the chamber 1210 while the second LDAP system is installed at the air outlet and serves to reduce the pathogen and dust loading coming out of the chamber 1210. In one embodiment, the HVAC system 1212 is the LDHPEC system 100 shown in FIG. 1. The LDHPEC system 100 includes the liquid desiccant evaporative cooler system 110, the liquid desiccant humidity recovery system 120, the storage system 130, the piping system 140, and the control system 150.

Figure 13:
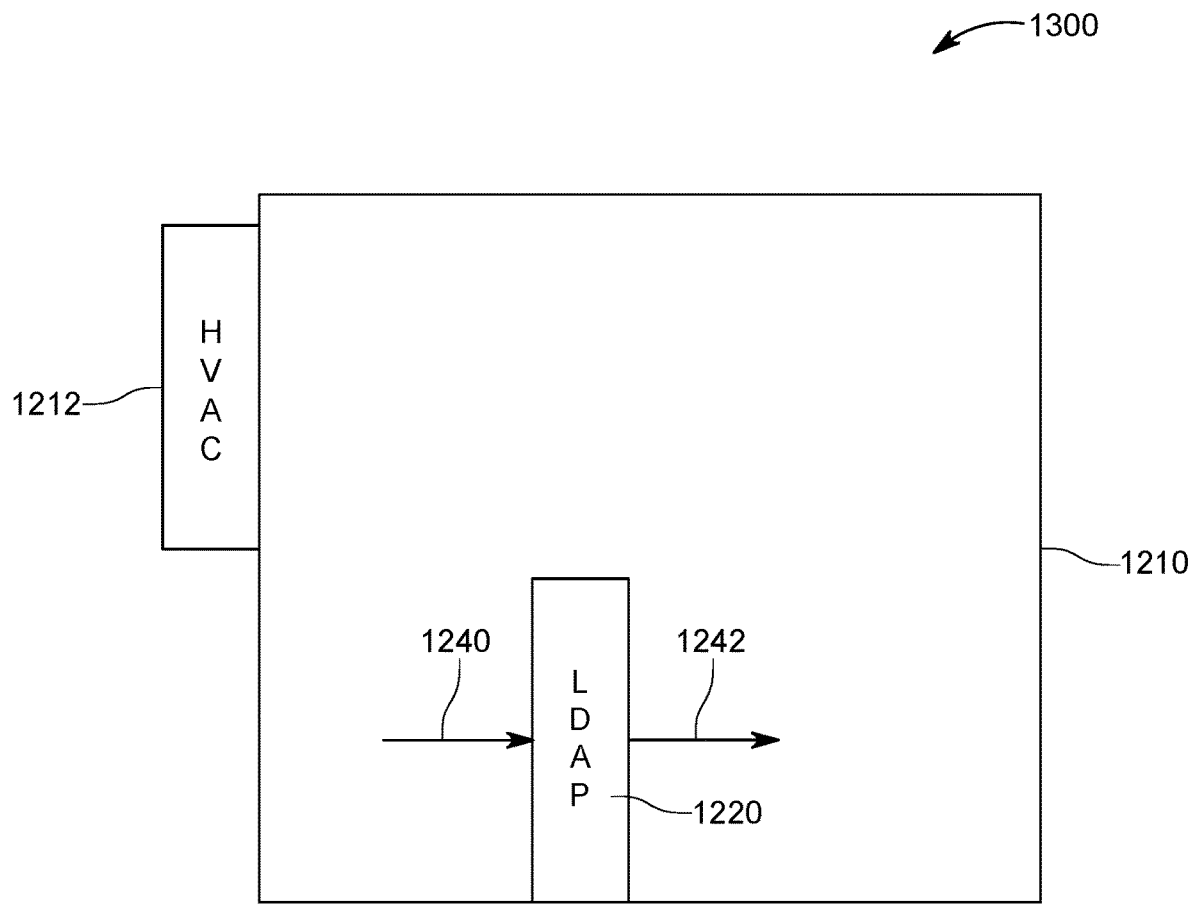
FIG. 13 illustrates a configuration in which the liquid desiccant based air purification system is used as a stand-alone system inside a chamber.

Alternatively, if the air inside the chamber 1210 is not desired to be refreshed on a continuous manner, as in the embodiment shown in FIG. 12, then it is possible to place one or more of the LDAP systems 1220 as standalone systems inside the chamber 1210, as illustrated in FIG. 13, and then the inlet air stream 1240 and the outlet air stream 1242 are confined to the interior of the chamber 1210. The HVAC system 1212 may still be used to cool the air inside the chamber 1210. As those skilled in the art would understand, using the LDAP systems in association with a chamber in which live stock or plants are grown is just one possible application of this air purification system. The LDAP system can be applied in any situation where the air needs to be purified.

In view of the severe consequences due to the outbreak of various diseases (e.g., avian flu) in the livestock industry, the LDAP systems discussed herein are expected to significantly improve the air quality for controlled environments, and is of special significance to the controlled environment agriculture industry, including the poultry industry. The LDAP systems discussed herein may be installed to purify incoming, recirculating, and/or exiting air streams from a controlled environment.

The disclosed embodiments provide an evaporative system combined with a humidity recovery system, both systems using liquid desiccants for controlling the temperature inside the enclosure and recycling the humidity inside the enclosure. An incoming air stream in the enclosure has humidity from the liquid desiccant added to it while the same humidity is recovered just before the air stream is discharged outside the enclosure. In addition, a liquid desiccant air purification system may be used as a standalone system or in combination with a liquid desiccant humidity pump and evaporative cooler system. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

REFERENCES

Davies, P. A. (2005). A solar cooling system for greenhouse food production in hot climates. Solar Energy 79, 661-668.

El Hourani, M., Ghali, K., and Ghaddar, N. (2014). Effective desiccant dehumidification system with two-stage evaporative cooling for hot and humid climates. Energy and Buildings 68, 329-338.

ESTPC (2012). ESTCP Cost and Performance Report: Solar Powered Liquid Desiccant Air Conditioner for Low-electricity Humidity Control (Environmental Security Technology Certification Program, U.S. Department of Defense).

Kassem, T. K., Alosaimy, A. S., Hamed, A. M., Fazian, M. (2013). Solar powered dehumidification systems using desert evaporative coolers: Review. International Journal of Engineering and Advanced Technology 3, 115-128.

Kozubal, E., Woods, J., Burch, J., Boranian, A., and Merrigan, T. (2011). Desiccant Enhanced Evaporative Air-Conditioning (DEVap): Evaluation of a New Concept in Ultra Efficient Air Conditioning (National Renewable Energy Laboratory).

Lefers, R. (2017). A Liquid Desiccant Cycle for Dehumidification and Fresh Water Supply in Controlled Environment Agriculture. In Water Desalination and Reuse Center (Thuwal, Saudi Arabia: King Abdullah University of Science and Technology).

Lefers, R., Bettahalli, N. M. S., Nunes, S. P., Fedoroff, N., Davies, P. A., and Leiknes, T. (2016). Liquid desiccant dehumidification and regeneration process to meet cooling and freshwater needs of desert greenhouses. Desalination and Water Treatment 57, 23430-23442.

Lowenstein, A. (2008). Review of Liquid Desiccant Technology for HVAC Applications. Hvac&R Research 14, 819-839.

Lychnos, G., and Davies, P. A. (2012). Modelling and experimental verification of a solar-powered liquid desiccant cooling system for greenhouse food production in hot climates. Energy 40, 116-130.

Mahmud, K., Mahmood, G. I., Simonson, C. J., and Besant, R. W. (2010). Performance testing of a counter-cross-flow run-around membrane energy exchanger (RAMEE) system for HVAC applications. Energy and Buildings 42, 1139-1147.

Mohammad, A. T., Bin Mat, S., Sulaiman, M. Y., Sopian, K., and Al-abidi, A. A. (2013a). Survey of hybrid liquid desiccant air conditioning systems. Renewable and Sustainable Energy Reviews 20, 186-200.

Mohammad, A. T., Mat, S. B., Sulaiman, M. Y., Sopian, K., and Al-Abidi, A. A. (2013b). Historical review of liquid desiccant evaporation cooling technology. Energy and Buildings 67, 22-33.

Oberg, V., and Goswami, D. Y. (1998). A review of liquid desiccant cooling. Advances in Solar Energy 12, 431-470.

Sabeh, N. C. (2007). Evaluating and Minimizing Water Use by Greenhouse Evaporative Cooling Systems in a Semi-Arid Climate. In Department of Agricultural and Biosystems Engineering (Tucson, Arizona: The University of Arizona).

Seyed-Ahmadi, M., Erb, B., Simonson, C. J., and Besant, R. W. (2009). Transient behavior of run-around heat and moisture exchanger system. Part I: Model formulation and verification. International Journal of Heat and Mass Transfer 52, 6000-6011

What is claimed is:

1. A liquid desiccant system for controlling a temperature inside an enclosure, the system comprising: a liquid desiccant evaporative cooler (LDEC) system configured to cool down an incoming air stream (AA) entering the enclosure by using a first liquid desiccant; a liquid desiccant humidity recovery (LDHR) system configured to remove humidity from a humid air stream (AD) that exists in the enclosure by using a second liquid desiccant; and a storage system fluidly connected to the LDEC system and to the LDHR system and configured to separately store the first liquid desiccant and the second liquid desiccant, wherein the humid air stream (AD) includes water vapors from the first liquid desiccant and from inside the enclosure.

2. The system of claim 1, wherein the storage system comprises a first storage tank that holds the first liquid desiccant and a second storage tank that holds the second liquid desiccant.

3. The system of claim 2, wherein the first liquid desiccant is lower in water vapor pressure than the second liquid desiccant.

4. The system of claim 3, wherein the LDEC system transfers humidity from the first liquid desiccant to the incoming air stream.

5. The system of claim 4, wherein the first liquid desiccant is fed from the first storage tank to the LDHR system, which is configured to transfer humidity from the humid air stream to the second liquid desiccant.

6. The system of claim 5, wherein the second liquid desiccant is fed from the second storage tank to the LDEC system.

7. The system of claim 1, further comprising:
a controller; and
plural sensors located at the LDEC system, the LDHR system, and the storage system.

8. The system of claim 7, wherein the controller compares a reading from one sensor of the plural sensors, indicative of a vapor pressure in the incoming air stream, with a reading from another sensor of the plural sensors, indicative of a vapor pressure of the first liquid desiccant, and determines to switch off a pump associated with the LDEC system.

9. The system of claim 7, wherein the controller compares a reading from one sensor of the plural sensors, indicative of a vapor pressure in the humid air stream, with a reading from another sensor of the plural sensors, indicative of a vapor pressure of the second liquid desiccant, and determines to switch off a pump associated with the LDHR system.

10. The system of claim 1, wherein the enclosure is a greenhouse, the incoming air stream is a hot and dry air stream, and the first and second liquid desiccants include salt water.

11. The system of claim 1, wherein the storage system is buried underground.

12. The system of claim 1, wherein the incoming air stream is taken from outside the enclosure and an output air stream of the LDHR system is discharged outside the enclosure.

13. A greenhouse having a liquid desiccant system for controlling a temperature inside the greenhouse, the greenhouse comprising:
a liquid desiccant evaporative cooler (LDEC) system attached to the greenhouse and configured to cool down an incoming air stream (AA) by using a first liquid desiccant;
a liquid desiccant humidity recovery (LDHR) system attached to the greenhouse and configured to remove humidity from a humid air stream (AD) by using a second liquid desiccant; and
a storage system fluidly connected to the LDEC system and to the LDHR system, the storage system being located outside the greenhouse, and configured to separately store the first liquid desiccant and the second liquid desiccant,
wherein the incoming air stream (AA) is taken from outside the enclosure, and the humid air stream (AD) includes water vapors from the first liquid desiccant and from plants located inside the greenhouse.

14. The greenhouse of claim 13, wherein the storage system comprises a first storage tank that holds the first liquid desiccant and a second storage tank that holds the second liquid desiccant, and wherein the first liquid desiccant is lower in water vapor pressure than the second liquid desiccant.

15. The greenhouse of claim 13, wherein the LDEC system transfers humidity from the first liquid desiccant to the incoming air stream, the first liquid desiccant is fed to the LDHR system, which is configured to transfer humidity from the humid air stream to the second liquid desiccant, and the second liquid desiccant is fed to the LDEC system.

16. The greenhouse of claim 13, further comprising:
a controller; and
plural sensors,
wherein the controller compares a reading from one sensor of the plural sensors, which is indicative of a vapor pressure in the incoming air stream, with a reading from another sensor of the plural sensors, which is indicative of a vapor pressure of the first liquid desiccant, and determines to switch off a pump associated with the LDEC system, or
the controller compares a reading from one sensor of the plural sensors, which is indicative of a vapor pressure in the humid air stream, with a reading from another sensor of the plural sensors, which is indicative of a vapor pressure of the second liquid desiccant, and determines to switch off a pump associated with the LDHR system.

17. The greenhouse of claim 13, wherein the first and second liquid desiccants include salt water.

* * * * *